US012594391B2

(12) United States Patent
Hendriks et al.

(10) Patent No.: US 12,594,391 B2
(45) Date of Patent: Apr. 7, 2026

(54) MODEL-GUIDED IMAGING FOR MECHANICAL VENTILATION

(71) Applicant: KONINKLIJKE PHILIPS N.V., Eindhoven (NL)

(72) Inventors: Cornelis Petrus Hendriks, Eindhoven (NL); Thomas Koehler, Hamburg (DE); Joerg Sabczynski, Hamburg (DE); Roberto Buizza, Eindhoven (NL); Rafael Wiemker, Hamburg (DE); Jaap Roger Haartsen, Eindhoven (NL); Michael Polkey, London (GB)

(73) Assignee: Koninklijke Philips N.V., Eindhoven (NL)

( * ) Notice: Subject to any disclaimer, the term of this patent is extended or adjusted under 35 U.S.C. 154(b) by 273 days.

(21) Appl. No.: 18/411,086

(22) Filed: Jan. 12, 2024

(65) Prior Publication Data

US 2024/0238545 A1     Jul. 18, 2024

Related U.S. Application Data

(60) Provisional application No. 63/438,557, filed on Jan. 12, 2023.

(51) Int. Cl.
*G06T 7/11* (2017.01)
*A61M 16/00* (2006.01)
(Continued)

(52) U.S. Cl.
CPC ......... *A61M 16/026* (2017.08); *G06T 7/0012* (2013.01); *G06T 7/11* (2017.01);
(Continued)

(58) Field of Classification Search
CPC ........ G16H 10/60; G16H 20/10; G16H 40/60; G16H 30/40; G16H 30/20; G16H 50/20;
(Continued)

(56) References Cited

U.S. PATENT DOCUMENTS 11,166,666 B2    11/2021  Raju
2007/0240717 A1*  10/2007  Kaczka ............... A61M 16/021
                                              128/204.21
(Continued)

OTHER PUBLICATIONS

Mouloud A. Denai et al.,"Absolute Electrical Impedance Tomography (aEIT) Guided Ventilation Therapy in Critical Care Patients: Simulations and Future Trends," Nov. 10, 2009, IEEE Transactions on Information Technology in Biomedicine, vol. 14, No. 3, May 2010, pp. 641-648.*

(Continued)

*Primary Examiner* — Omar S Ismail

(57) ABSTRACT

A mechanical ventilation assessment assistance device includes at least one electronic processor; and a non-transitory storage medium storing instructions readable and executable by the at least one electronic processor to perform a mechanical ventilation assessment assistance method including obtaining an image of a patient (P) receiving mechanical ventilation; generating or updating a patient-specific lung model of at least one lung of the patient based on the obtained image; simulating a response of the patient to a mechanical ventilation therapy using the generated or updated patient-specific lung model; comparing the simulated response with an actual response of the patient to the mechanical ventilation therapy; based on the comparison, determining an imaging recommendation for acquiring an image of at least one lung of the patient; and outputting the determined imaging recommendation.

14 Claims, 4 Drawing Sheets

(51) Int. Cl.
　　 *G06T 7/00* 　　　　 (2017.01)
　　 *G16H 50/50* 　　　 (2018.01)
(52) U.S. Cl.
　　 CPC ... *G16H 50/50* (2018.01); *G06T 2207/10072*
　　　　 (2013.01); *G06T 2207/10132* (2013.01); *G06T*
　　　　　　　　　　　　　　 *2207/30064* (2013.01)
(58) Field of Classification Search
　　 CPC ......... G16H 50/50; A61M 16/00; G06T 7/00;
　　　　　　　　　　　　　　　　　　　　 G06T 7/11
　　 See application file for complete search history.

(56)　　　　　　 References Cited

U.S. PATENT DOCUMENTS

| | | | |
|---|---|---|---|
| 2008/0281219 A1* | 11/2008 | Glickman | A61M 16/024 |
| | | | 600/533 |
| 2012/0041279 A1* | 2/2012 | Freeman | A61B 5/0803 |
| | | | 600/534 |
| 2015/0150482 A1* | 6/2015 | Fouras | A61B 5/1128 |
| | | | 600/407 |
| 2016/0339019 A1* | 11/2016 | Laberge | A61P 9/10 |
| 2016/0339191 A1* | 11/2016 | Kaczka | A61M 16/0096 |
| 2017/0266211 A1* | 9/2017 | David | A61K 31/675 |
| 2018/0280646 A1* | 10/2018 | Freeman | A61M 16/024 |
| 2019/0336539 A1* | 11/2019 | Wallace | A61P 25/28 |
| 2020/0305759 A1* | 10/2020 | Barash | A61B 5/0816 |
| 2020/0329977 A1* | 10/2020 | Freeman | A61B 5/7278 |
| 2020/0383647 A1* | 12/2020 | Freeman | A61B 5/7264 |
| 2021/0205561 A1* | 7/2021 | Eger | A61B 5/0803 |
| 2022/0339382 A1* | 10/2022 | Eger | G16H 50/50 |
| 2022/0379057 A1* | 12/2022 | Eger | G16H 40/40 |
| 2023/0044025 A1* | 2/2023 | Trujillo | A61K 38/57 |
| 2023/0102865 A1* | 3/2023 | Hendriks | A61B 5/08 |
| | | | 128/204.23 |
| 2023/0133374 A1 | 5/2023 | Muller | |

OTHER PUBLICATIONS

Daniel Lichtenstein et al., "Comparative Diagnostic Performances of Auscultation, Chest Radiography, and Lung Ultrasonography in Acute Respiratory Distress Syndrome," Anesthesiology, V 100, No. 1, Jan. 2004, pp. 9-14.*

Jacob Herrmann et al., "Assessment of Heterogeneity in Lung Structure and Function During Mechanical Ventilation: A Review of Methodologies," May 11, 2022, Journal of Engineering and Science in Medical Diagnostics and Therapy, Nov. 2022, vol. 5, pp. 040801-1-040801-8.*

Steffen Leonhardt et al.,"Electrical impedance tomography: the holy grail of ventilation and perfusion monitoring?," Sep. 20, 2012, Intensive Care Med (2012) 38, pp. 1917-1925.*

Roth, C.J. et al., "A comprehensive computational Human Lung model incorporating inter-acinar dependencies: Applicaiton to spontaneous breathing and mechanical ventilation", (2017), Int. J. Numer. Met Biomed. Engng.

Brogi, E. et al., 2017, "Could the use of bedside lung ultrasound reduce the number of chest x-rays in the intensive care unit?", Cardiovasc Ultrasound. Sep. 13, 2017;15(1):23.

Scott, J. et al., 2021, "Restricting Daily Chest Radiography in the Intensive Care Unit: Implementing Evidence-Based Medicine to Decrease Utilization", J Am Coll Radiol., Mar. 2021;18(3 Pt A):354-360.

Lichtenstein, D. et al., 2004, "Comparative diagnostic performances of auscultation, chest radiography, and lung ultrasonography in acute respiratory distress syndrome", Anesthesiology, Jan. 2004;100(1):9-15.

International Search Report for PCT/EP2024/050187 filed Jan. 5, 2024.

Denai, M.A. et al., "Absolute Electrical Impedance Tomography (aEIT) Guided Ventilation Therapy in Critical Care Patients: Simulations and Future Trends", IEEE Transactions on Information Technology in Biomedicine, vol. 14, No. 3, (May 1, 2010), pp. 641-649.

Leonhardt, S. et al. , "Electrical impedance tomography: the holy grail of ventilation and perfusion monitoring?", Intensive Care Medicine, vol. 38, No. 12, (Sep. 20, 2012), pp. 1917-1929.

Morton, S.E. et al., "Optimising mechanical ventilation through model-based methods and automation", Annual Reviews in Control, , vol. 48, (Jan. 1, 2019), pp. 369-382.

* cited by examiner

100

111

117

Obtain image
102

Generate or
update model
104

Simulate MV
with model 106

Provide MV 108

Patient
responding
well? 110

No

Yes

Generate map
112

Output map 114

US images 116

MODEL-GUIDED IMAGING FOR MECHANICAL VENTILATION

CROSS-REFERENCE TO RELATED APPLICATIONS

This patent application claims the priority benefit under 35 U.S.C. § 119(e) of U.S. Provisional Application No. 63/438,557, filed on Jan. 12, 2023, the contents of which are herein incorporated by reference.

The following relates generally to the pulmonology arts, mechanical ventilators, the mechanical respiratory therapy arts, mechanical ventilator configuration or setup, respiratory modeling arts, Ventilator Induced Lung Injury (VILI) prevention arts, and related arts.

BACKGROUND

During mechanical ventilation therapy of a patient, clinicians decide the volume of air (e.g. per breath) that a mechanical ventilator is to provide to the patient based on body size of the patient. This volume needs to provide sufficient aeration without causing damage to the lung due to stress (barotrauma), strain (volutrauma), or shear due to cyclic opening and collapse of the alveoli (atelectrauma). This type of lung damage due to the stresses and strains imposed by the mechanical ventilator is known as Ventilator Induced Lung Injury (VILI).

A problem in determining the mechanical ventilator settings for preventing lung damage is that the lung is heterogeneous, either intrinsically due to locally varying structures, geometry, and mechanical properties, or secondarily due to local damage or fluid accumulation caused by a disease or infection such as chronic obstructive pulmonary disease (COPD), pneumonia, edema, Covid-19, fibrosis, and so forth. This heterogeneity of the lungs can lead to local stress and strain concentrations that are much higher than the apparent (e.g. average or global) stress and strain estimated based on the patient's body size, or based on the lumped volume and compliance as measured by mechanical ventilators.

In some current approaches, a solution for the assessment and prevention of VILI includes constructing a three-dimensional (3D) biophysical model of a patient's lungs based on computed tomography (CT) exhalation imaging information of the patient (see, e.g., Roth, J. et al., 2017, "A comprehensive computational human lung model incorporating inter-acinar dependencies: Application to spontaneous breathing and mechanical ventilation", Int. J. Numer. Meth. Biomed. Engng. (2017); e02787). With this model constructed using the CT imaging of the patient, the clinician can virtually test various mechanical ventilator (MV) settings and see via simulation what happens in the lung (e.g., a strain distribution in the parenchymal tissue). The mechanical properties of the lung tissue (i.e., the stiffness of the alveolar ducts and the inter alveoli linkers) are chosen such that the lung model simulates experimental behavior. In this approach, the mechanical properties are not patient specific and not locally varying. The model of the patient's lungs generated using the CT images of the patient is sometimes referred to as a digital twin, as it is a digital representation of the physical lungs of the patient.

The following discloses certain improvements.

SUMMARY

In one aspect, a mechanical ventilation assessment assistance device includes at least one electronic processor; and a non-transitory storage medium storing instructions readable and executable by the at least one electronic processor to perform a mechanical ventilation assessment assistance method including obtaining an image of a patient receiving mechanical ventilation; generating or updating a patient-specific lung model of at least one lung of the patient based on the obtained image; simulating a response of the patient to a mechanical ventilation therapy using the generated or updated patient-specific lung model; comparing the simulated response with an actual response of the patient to the mechanical ventilation therapy; based on the comparison, determining an imaging recommendation for acquiring an image of at least one lung of the patient; and outputting the determined imaging recommendation.

In another aspect, a mechanical ventilation assessment assistance method includes, with at least one electronic processor: obtaining an image of a patient receiving mechanical ventilation; generating or updating a patient-specific lung model of at least one lung of the patient based on the obtained image; simulating a response of the patient to a mechanical ventilation therapy using the generated or updated patient-specific lung model; comparing the simulated response with an actual response of the patient to the mechanical ventilation therapy; based on the comparison, determining an imaging recommendation for acquiring an image of at least one lung of the patient; and outputting the determined imaging recommendation.

One advantage resides in providing a model of the lungs of a patient undergoing mechanical ventilation therapy having mechanical properties with heterogeneous tissue stiffness, patient-specific, and calibrated mechanical properties.

Another advantage resides in providing a model of the lungs of a patient undergoing mechanical ventilation therapy with tissue map sections corresponding to mechanical properties of the lungs.

Another advantage resides in providing a map of the lungs of a patient undergoing mechanical ventilation therapy on a display device of a mechanical ventilator, thereby reducing the need for an additional computer in an intensive care unit (ICU).

Another advantage resides in providing a map generated from a model of a patient undergoing mechanical ventilation therapy overlaid with a radiation image of a patient on a display device of a mechanical ventilator.

Another advantage resides in selecting portions of lungs of a patient undergoing mechanical ventilation therapy to be imaged by an ultrasound device rather than a radiation imaging device.

Another advantage resides in reducing ionizing radiation exposure to a patient undergoing mechanical ventilation therapy.

Another advantage resides in a quick lung ultrasound scan.

Another advantage resides in allowing ultrasound technicians, rather than radiation imaging technicians, to acquire images of lungs of a patient.

Another advantage resides in reduced imaging costs.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
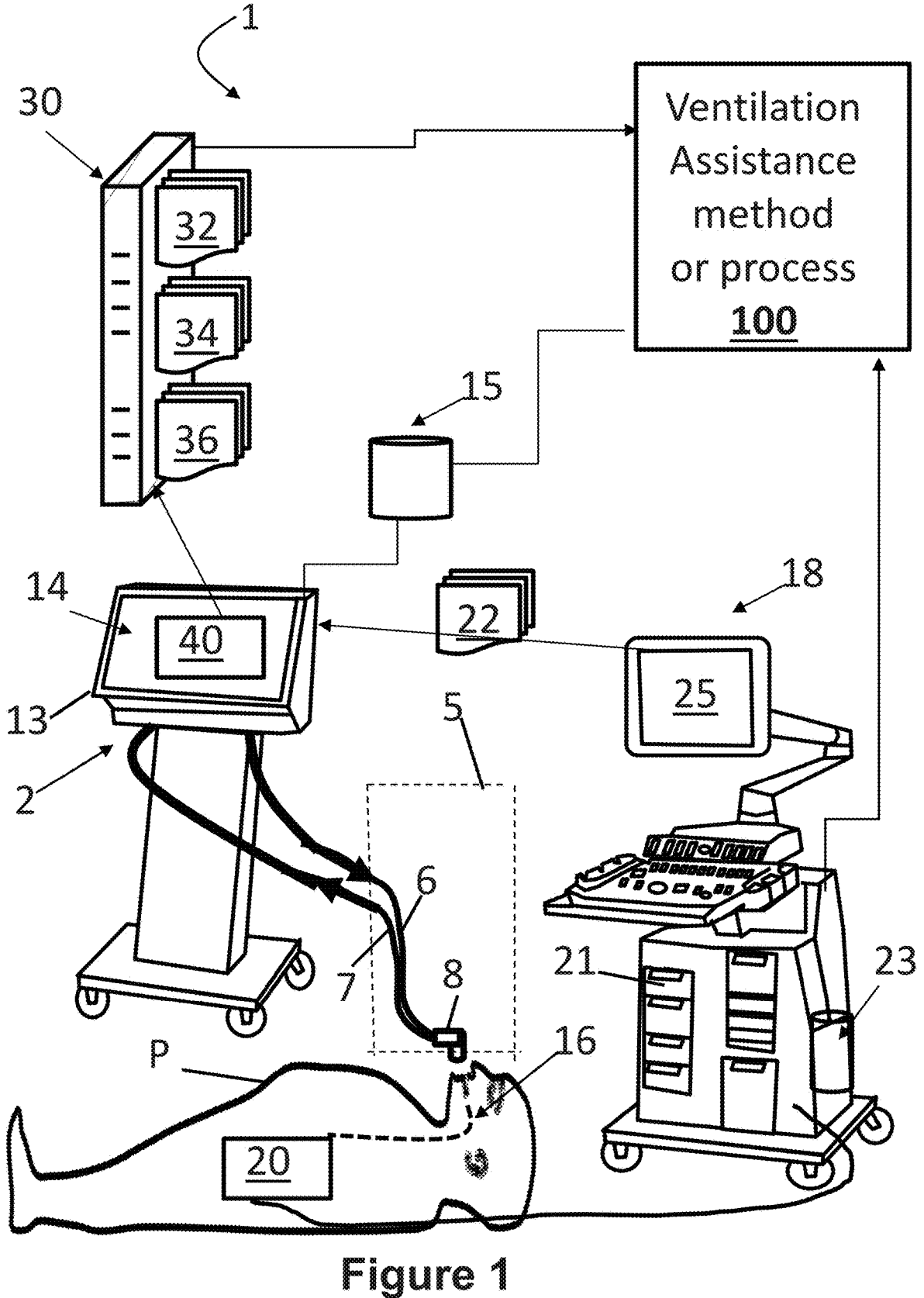
FIGS. 1 and 2 diagrammatically show an illustrative mechanical ventilation system in accordance with the present disclosure.

As used herein, the singular form of "a," "an," and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by the same item of hardware.

CT imaging based digital twin simulations can support decisions on a personalized protective ventilation scenario. However, for example, when a patient has been in the ICU for a while then the condition of the patient's lungs may have changed (either improved or deteriorated or improved in some respect but deteriorated in another respect), and hence it might be needed to take a new CT scan for diagnostic reasons or to adjust the mechanical ventilation therapy. However, a CT scan with ICU patients, especially, when being sedated, is challenging.

Disclosed herein are systems and methods to support bedside clinicians and care providers in providing safe mechanical ventilation, including guiding clinicians in selecting ventilator settings that will not produce VILI in the specific patient. However, acquiring CT or 3D or multi-view X-ray images of the patient may not be feasible or advisable, for example due to a desire to avoid ionizing radiation exposure of an at-risk patient, difficulty in positioning an unconscious patient, exigency of a clinical emergency situation, or so forth. In these cases, the usual approach for constructing a patient-specific digital twin for configuring the mechanical ventilator is not feasible, due to the lack of access to CT or 3D or multi-view X-ray images of the patient.

In embodiments disclosed herein, this type of situation is addressed by constructing a patient-specific digital twin of the patient's lungs based on CT or 3D or multi-view X-ray imaging data for a similar patient. Alternatively, if a digital twin of a similar patient is available then this digital twin can be directly adjusted to the current patient.

The disclosed approaches in some embodiments employ using the digital twin of the patient for use in determining the mechanical ventilator settings. A map of the patient's lung is generated from the digital twin, with specific locations in the lungs being selected for ultrasound imaging, as opposed to acquiring additional radiation images of the patient.

Some embodiments further provide a user interface (UI) with an easily read display. The model output is translated in actionable clinical decision support (CDS) information. The user interface (UI) of the mechanical ventilator shows options for the clinician to decide from.

The following discloses a system to reduce the time needed for lung ultrasound. A patient digital model generates output to support the therapist with managing the ventilator settings and to decide on the imaging modality, and to guide the sonographer with a lung ultrasound scan or patch. The model output can be shown in the user interface of a computer or any one of the devices connected to the patient. The decision algorithm can also take as input cardiopulmonary simulation outputs and measurements.

Figure 2:
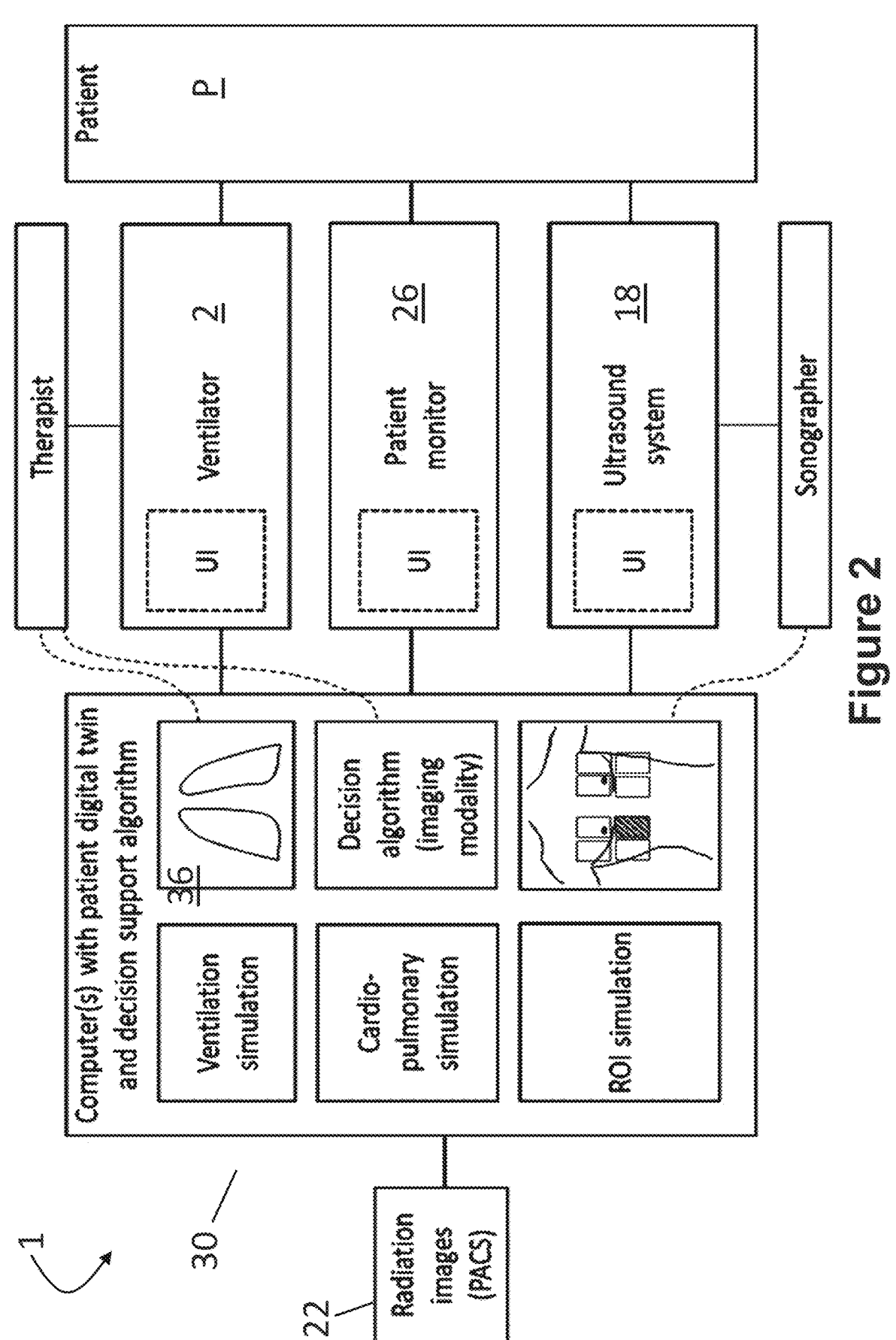

With reference to FIGS. 1 and 2, a mechanical ventilation assessment assistance device or system 1 includes a mechanical ventilator 2 for providing ventilation therapy to an associated current patient P is shown. As shown in FIG. 1, the mechanical ventilator 2 is connected with a patient breathing circuit 5 to delivery mechanical ventilation to the current patient P. The patient breathing circuit 5 includes typical components for a mechanical ventilator, such as an inlet line (i.e., inhalation limb) 6, an optional outlet line (exhalation limb) 7 (this may be omitted if the ventilator employs a single-limb patient circuit), a connector or port 8 for connecting with an endotracheal tube (ETT) or other patient respiratory interface device, and one or more breathing sensors (not shown), such as a gas flow meter, a pressure sensor, end-tidal carbon dioxide (etCO$_2$) sensor, and/or so forth. The mechanical ventilator 2 is designed to deliver air, an air-oxygen mixture, or other breathable gas (supply not shown) to the inhalation limb 6 of the patient breathing circuit 5 at a programmed (and typically time-varying) pressure and/or flow rate to ventilate the patient via an ETT. The mechanical ventilator 2 also includes an electronic controller (e.g., a microprocessor) 13 for controlling operation of the mechanical ventilator 2, and a display device 14 for displaying information about the current patient P and/or settings of the mechanical ventilator 2 during mechanical ventilation of the current patient P, and a non-transitory computer readable medium 15 storing instructions executable by the electronic controller 13.

FIG. 1 diagrammatically illustrates the current patient P intubated with an ETT 16 (most of which is inside the current patient P and hence is shown in phantom). The connector or port 8 connects with the ETT 16 to operatively connect the mechanical ventilator 2 to deliver breathable air via the inhalation limb 6 to the current patient P via the ETT 16, and to transport exhaled air back to the ventilator (or to another discharge) via the exhalation limb 7. The mechanical ventilation provided by the mechanical ventilator 2 via the ETT 16 may be therapeutic for a wide range of conditions in which the patient P requires breathing assistance or is wholly unable to spontaneously breath, such as various types of pulmonary conditions like emphysema or pneumonia, viral or bacterial infections impacting respiration such as a COVID-19 infection or severe influenza, cardiovascular conditions in which the current patient P receives breathable gas enriched with oxygen, or so forth.

FIG. 1 also shows a medical imaging device 18 (also referred to as an image acquisition device, imaging device, and so forth). The image acquisition device 18 can be a two-dimensional (2D) X-ray imaging device or an ultrasound (US) image acquisition device, for example. As primarily described herein, the medical imaging device 18 comprises a US medical imaging device 18 (i.e., a bedside US imaging device). An ultrasound imaging device is a typical choice for a patient who is not a good candidate for CT or 3D or multi-view X-ray imaging due to being at-risk for ionizing radiation exposure, lacks mobility, or requires urgent mechanical ventilation therapy. Another option is a 2D X-ray imaging device such as a direct digital radiograph (DDR) imaging device, which acquires a single planar X-ray image of the current patient P. While portable, as primarily described herein, the medical imaging device 18 comprises a US imaging device with an ultrasound transducer 20 configured to acquire US images 22 of a diaphragm of the patient P. The US imaging device 18 can be a bedside imaging device. In some embodiments, the electronic controller 13 can be implemented in the US imaging device 18.

For purposes of bedside monitoring of a patient to assess effectiveness of mechanical ventilation and/or onset of VILI, portable ultrasound advantageously provides low-cost imaging easily deployed in an ICU or other patient location. Coupling of the ultrasound imaging device 18 to the patient merely entails positioning the ultrasound transducer 18 (which may be a handheld device or strapped to the patient) on the torso of the patient P in proximity to the lung to be imaged. This can be repeated to image the left and right lungs (or right and left lungs) in succession. Advanced ultrasound imaging data analysis techniques such as lung sliding analysis can also provide additional clinically relevant information.

However, ultrasound imaging has some disadvantages for the purpose of assessing effectiveness of mechanical ventilation and/or onset of VILI. Ultrasound can only image superficial parts of the lung, and some clinically relevant features may not have strong contrast in ultrasound images. Hence, ultrasound images are often not sufficient to construct a "digital twin" of the lungs of the patient P for use in modeling the mechanical ventilation.

Hence, it may be advisable to perform (follow-up) X-ray imaging to provide images of the entire lung and/or complementary information about the condition of the lungs. X-ray imaging may provide stronger contrast for some clinically significant features that could be missed in ultrasound imaging. However, X-ray imaging is not as convenient as ultrasound imaging. Ultrasound imaging is local (i.e., it takes quite long to get an image of the entire lung) and ultrasound imaging cannot penetrate lung tissue, (i.e., it provides only information about superficial structures of the lung). Advanced X-ray imaging modalities such as computed tomography (CT) imaging scanners can provide 3D tomographic images sufficient data to construct a "digital twin" of the lungs—but a CT scanner is not portable, so a bedridden patient must be transported to the radiology department and loaded into the CT scanner for CT imaging. Portable X-ray imaging systems are available which can avoid the necessity to transport the patient to the imaging device. However, portable X-ray imaging usually only acquires a 2D X-ray image (or at most a number of discrete 2D views), and still requires positioning the X-ray tube and the X-ray detector on opposite sides of the patient so the X-rays pass from the X-ray tube through the patient to the X-ray detector. Bedside X-ray imaging thus usually involves lifting the patient to place a flatpanel X-ray detector underneath the patient, which is less convenient than the use of the handheld or strapped-on ultrasound transducer 20. In addition, C-arm imaging systems include an X-ray tube and X-ray detector mounted on opposite ends of a C-shaped suspension system. The suspension system can rotate around the patient. Thus, it is easily possible to acquire images from a multitude of orientations. It is even possible to reconstruct these into a 3D image (similar to CT imaging). They are often used in surgery. Nevertheless, many of these systems are mobile and can in principle be used at the bedside. However, there are some drawback, such as being much bigger and heavier than portable X-ray system used in the ICU today. In addition, in order to allow for a nice 3D reconstruction the X-ray absorption of the bed must not be too high, and is more expensive.

Hence, it is desirable to employ ultrasound imaging for daily (or more frequent) assessment of mechanical ventilation and/or onset of VILI; but to still ensure follow-up X-ray imaging is performed when clinically advisable. Moreover, when ultrasound imaging is employed for daily assessment, it is desirable to use optimal settings and ultrasound transducer placement to ensure fast and effective ultrasound assessment. Embodiments disclosed herein provide automated assistance for determining and providing a follow-up imaging recommendation for lung function assessment and early VILI onset detection, such as recommending follow-up ultrasound or X-ray imaging, and if the former also a recommendation of optimal ultrasound settings.

In one example, the medical imaging device 18 includes an electronic processor 21 configured to control the ultrasound imaging device 18 to acquire the US images 22, and also includes a non-transitory computer readable medium 23 storing instructions executable by the electronic processor 21 for determining the imaging recommendation. The medical imaging device 18 can also include a display device 25 for presenting information including the imaging recommendation. In another example, the electronic processor 13 of the mechanical ventilator 2 controls the ultrasound imaging device 18 to receive the ultrasound imaging data 22 of, for example, the diaphragm of the patient P from the US probe 20. The ultrasound probe 20 may allow for continuous and automatic acquisition of the ultrasound imaging data 22.

The patient P may optionally also be monitored by a patient monitor 26 (shown diagrammatically only in FIG. 2), such a multifunction patient monitor that monitors vital signs such as heart rate, respiration rate, blood pressure, blood oxygenation (e.g. $SpO_2$), capnography (i.e., carbon dioxide level in respired air), and/or so forth. Where available, the patient monitoring data acquired by the patient monitor 26 can also be leveraged in determining the imaging recommendation. For example, if the vital signs indicate the patient's heart rate is higher than desirable then this could indicate (along with other available data) that the lung functioning is deficient, and follow-up X-ray imaging should be recommended.

FIGS. 1 and 2 also show a server computer or electronic processor 30 storing a previously-acquired CT (or electrical impedance tomography (EIT), or X-ray, or ultrasound, magnetic resonance imaging (MRI), single photon emission computed tomography (SPECT), or positron emission tomography (PET)) image 32 of the patient P, a plurality of previously-acquired (i.e., historical) CT scans 34, and/or a plurality of patient-specific mechanical ventilation models 36 for other patients. The patient-specific mechanical ventilation models 36 can comprise, for example, an anatomical model, an artificial neural network (ANN) or other machine learning (ML) based model, and so forth.

The patient-specific mechanical ventilation models 36 are also referred to herein as a "digital twin" of the lungs. In some mechanical ventilation therapy sessions, there might be rare instances when it is desirable to develop and apply a protective ventilation scenario with a digital twin model. Provided with a sufficiently large library of imaging and other clinical data that is available and accessible, the server computer 30 is configured is to search a similar patient, take the digital twin of the similar patient, and personalize this model for the current patient P using the patient image 32 which is adjusted to the current patient P. The patient-specific mechanical ventilation models 36 can be a mesh-based model, but do not need to be a mesh-based model. The patient-specific mechanical ventilation models 36 comprise imaging-based patient-specific biophysical models, providing insight in heterogeneous lung deformation and flow. This may include the use of meshless approaches, mathematical models, machine learning, data analytics, etc.

The non-transitory computer readable medium 15 of the mechanical ventilator 2 and/or the non-transitory computer readable medium 23 of the US imaging device 18 and/or the server computer 30 stores instructions executable by the electronic controller 13 (and/or the electronic processor 21 and/or the server computer 30) to perform a mechanical ventilation assessment assistance method or process 100. Although primarily described in terms of the electronic controller 13/non-transitory computer readable medium 15 of the mechanical ventilator 2, the method 100 can similarly be performed by the electronic processor 21/non-transitory computer readable medium 23 of the US imaging device 18 and/or the server computer 30.

Figure 3:
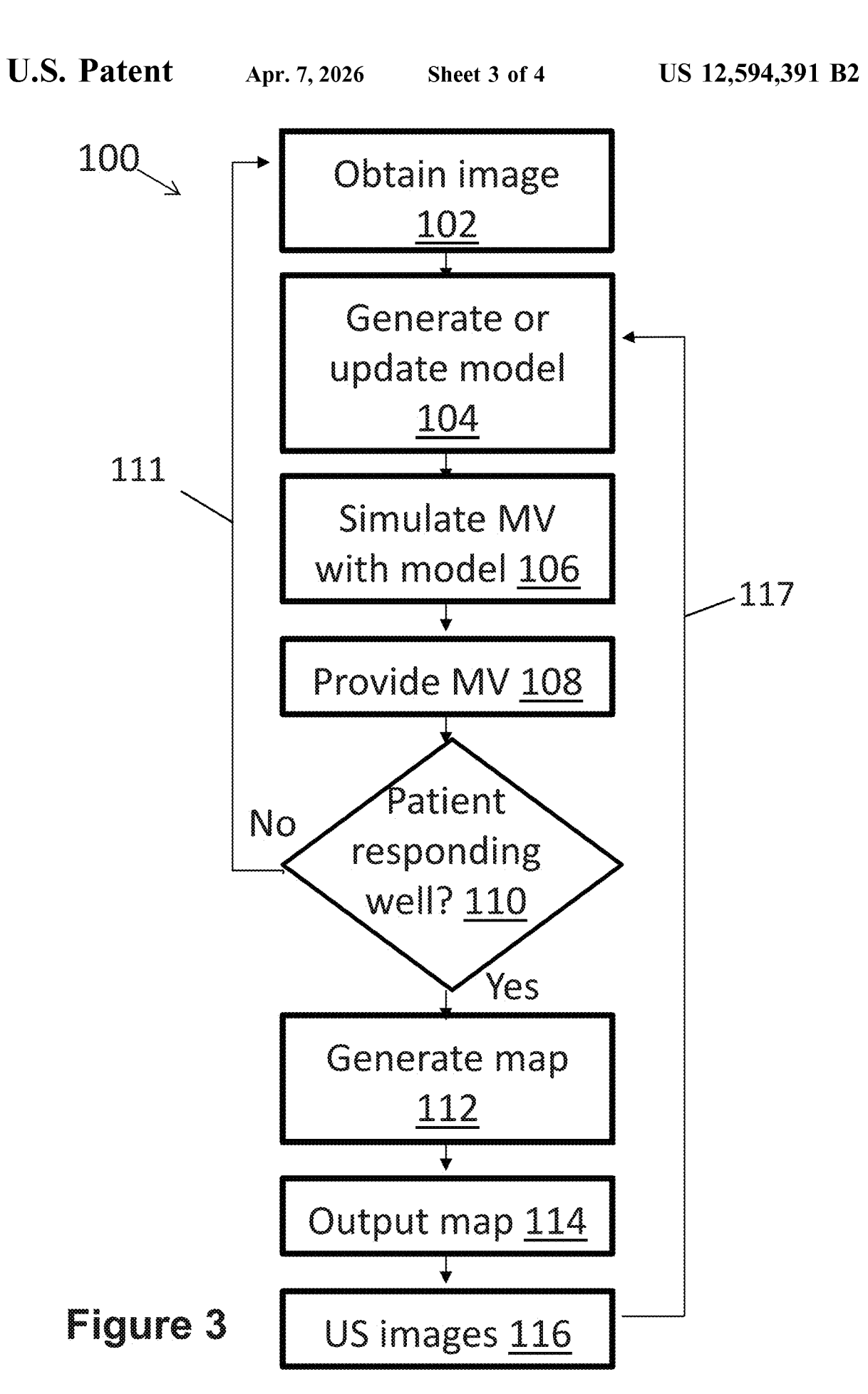
FIG. 3 shows an example flow chart of operations suitably performed by the system of FIGS. 1 and 2.

With reference to FIG. 3, and with continuing reference to FIGS. 1 and 2, an illustrative embodiment of the mechanical ventilation assessment assistance method 100 is diagrammatically shown as a flowchart. To begin the method 100, the patient P is intubated with the ETT 16. At an operation 102, the image 32 of the patient P is obtained while the patient P is receiving mechanical ventilation via the mechanical ventilator 2. To do so, the image 32 is obtained via an imaging device (not shown), or from the server computer 30. In some embodiments, the obtained image 32 includes a spectral CT or EIT image. The image 32 can comprise a, for example, 3D thoracic CT scan of the patient P.

At an operation 104, a patient specific lung model 36 of at least one lung of the patient P is generated or updated based on the obtained image 32. This can be done in a variety of manners. In some example embodiments, one or more lung lesions are identified in the obtained image 32, and the patient-specific lung model 36 of the patient P can be generated or updated to include the identified one or more lung lesions. In other example embodiments, fluid in at least one lung is identified in the obtained image 32, and the patient-specific lung model 36 of the patient P can be generated or updated to include the identified fluid. In other example embodiments, at least one value of at least one biophysical parameter (e.g., lung volume, air flow, and so forth) of at least one lung region of the patient P is determined using the obtained image 32, and the patient-specific lung model 36 of the patient P can be generated or updated to include the determined at least one value. In other example embodiments, a perfusion distribution in at least one lung of the patient P is identified using the obtained image 32 (i.e., a spectral CT or EIT image), and the patient-specific lung model 36 of the patient P can be generated or updated to include the identified perfusion distribution.

The model 36 can also include a cardiopulmonary model of the patient to simulate physiological parameters such as gas exchange and vital signs [see, e.g., Raju, B. I. et al., 2021, "Enhanced acute care management combining imaging and physiological monitoring", U.S. Pat. No. 11,166,666]. The patient-specific lung model 36 can have multiple "layers", such as (i) an anatomical model with segmentations (e.g., airways, bronchi, lobes, lesions, etc.). If necessary, meshes can be created from these segmentations, either triangular or polygonal for 2D) surfaces or polyhedrical meshes for 3D bodies in finite element modeling; (ii) a functional model with, for example, ventilation, strain, compliance, or a perfusion distribution, etc. The functional model can be constructed with biophysical simulations or image processing techniques such as deformable image registration (Jacobian matrix); and (iii) a 3D map with diagnostic findings such as lesions, pneumothorax, water etc. as determined by radiological examinations (digital annotations and mark ups), CT physics, and/or artificial intelligence (AI).

At an operation 106, a response of the patient P to a mechanical ventilation therapy using the mechanical ventilator 2 is simulated using the generated or updated patient-specific lung model 36. To do so, the server computer 30 is configured to simulate operation of the mechanical ventilator 2 delivering mechanical ventilation with the current ventilator settings to the lung model 36 to provide an expected patient response to the mechanical ventilation therapy to the patient P. In some examples, the patient-specific lung model 36 simulates the ventilation in the lungs and the blood flow in the cardiopulmonary system as a function of the mechanical ventilator settings. The simulated MV settings may be varied to simulate expected response of the patient P to the varied settings (advantageously without actually applying those "test" settings to the patient P), and the therapist selects the optimal setting by evaluating the simulation output. In another embodiment, the electronic processor 30 may automatically select the optimal setting. For example, a positive end-expiratory pressure (PEEP) setting can be selected such that the local strain in the patient's lungs as indicated by the ventilation simulation do not exceed 200%.

At an operation 108, the electronic controller 13 controls operation of the mechanical ventilator to employ the therapist-selected (or automatically selected) optimal settings to provide the mechanical ventilation therapy to the patient P to determine an actual response of the patient, which can be compared to the simulated response from the operation 106. In some embodiments, ventilator settings of the mechanical ventilator 2 applying the mechanical ventilation therapy to the patient P can be automatically updated when the actual response of the patient P to the applied mechanical ventilation therapy does not satisfy a predetermined criterion. The mechanical ventilation therapy with the updated settings can then be applied to the patient P. These operations 102-108 can be repeated until the actual response of the patient P exceeds the predetermined criterion. For example, the patient P is treated (i.e., ventilated) with the selected PEEP and the response of the patient P is monitored with patient monitoring system 26.

At an operation 110, an imaging recommendation 40 can be determined, based on results of the comparing operation 108, for acquiring an image of at least one lung of the patient P. The determined imaging recommendation 40 can be (i) a recommendation to acquire an ultrasound image 22 of the patient P if the comparison of the simulated response with the actual response of the patient to the mechanical ventilation therapy satisfies the predetermined criterion, or (ii) a recommendation to acquire a different image type (e.g., CT, X-ray, EIT, and so forth) of the patient P otherwise. This is based on the expectation that if the actual patient response agrees sufficiently well with the simulation, then it is likely the patient-specific lung model 36 is still a reasonably accurate representation of the patient's lungs. On the other hand, if the actual patient response deviates significantly from the simulation, then it is likely the patient-specific lung model 36 needs to be updated, and to this end the recommendation may be to acquire a new X-ray image which can then be used to update the patient-specific lung model 36 (this is indicated by flowback path 111 in FIG. 3). In some embodiments, one or more patient-specific ultrasound imaging settings (e.g., spatial locations in the lungs to be imaged) can be determined, and the recommendation 40 can include a recommendation to acquire an ultrasound image 22 of the patient using the determined one or more patient-specific ultrasound imaging settings.

In a particular example, the electronic controller 13 implements a decision algorithm takes as input the simulation and measurement results. In case the patient P is stable or improving, and there is no significant difference between the simulation and measurement output, (for example, less than 10%), it is recommended to follow-up the patient P with ultrasound. In case the patient P is not responding as expected (i.e., by therapist decision/input), or in case the simulations and measurements differ, for example, by greater than 10%, it is recommended to follow-up the patient P with radiation imaging (X-ray or CT) to see if the model 36 and/or therapist are overlooking or missing an unexpected event in the patient's lungs, e.g., an exacerbation or an infection.

At an operation 112, the determined imaging recommendation 40 can be output (for example, on the display device 14 of the mechanical ventilator 2 and/or the display device 25 of the US imaging device 25). In some embodiments, the determined imaging recommendation 40 can comprise a map including one or more regions of interest (ROI) in the obtained image 32 that is generated when the actual response of the patient P to the applied mechanical ventilation therapy satisfies a predetermined criterion. The map 40 can comprise a 3D map with ROIs for the lung ultrasound investigation (i.e., existing lesions, water or fluid, at-risk areas (e.g., areas with a simulated strain of greater than 200%), atelectasis, etc.).

At an operation 114, the generated map 40 is then displayed on the display device 14 of the mechanical ventilator 2 and/or the display device 25 of the US imaging device 25. In some examples, the obtained image 32 can be displayed on the display device 14 of the mechanical ventilator 2 and/or the display device 25 of the US imaging device 25, and the generated map 40 is then overlayed on the obtained image 32. One or more of the ROIs in the map 40 can be highlighted. A clinician can then provide one or more inputs indicative of a selection of one or more of the ROIs (i.e., the clinician can tap the display device screen to select one of the ROIs), and additional information related to the selected ROI can be displayed.

The 3D map 40 can be projected along with one or more 2D projections/tables (with positions) of the chest with scanning schemes to guide the sonographer. The projections/tables can have 4 zones, 6 zones, 8 zones, 10 zones, 12 zones, 24 zones or even more. The zones with an ROI (i.e., a lesion or areas with a high risk) are highlighted, and the ultrasound settings are mentioned.

In some embodiments, the 3D map 40 with ROIs is projected in a 2D projection of the chest with one or more tracks covering the ROIs. The sonographer then needs to wipe the ultrasound probe 20 over this predetermined track. Further methods to show the tracks to the sonographer could also be used (e.g., Augmented Reality, Virtual Reality, or other graphical means) to show the tracks.

Figure 4:
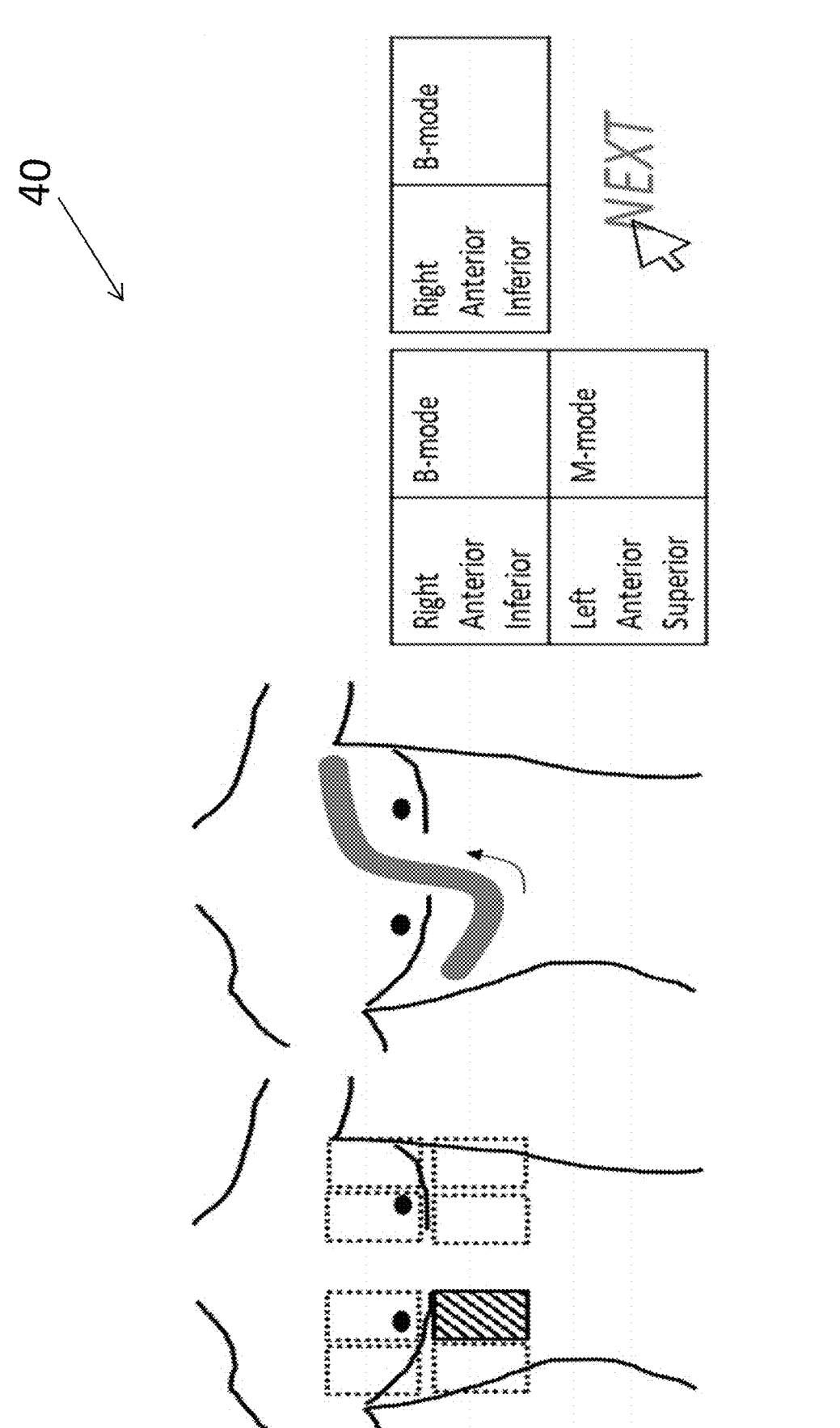
FIG. 4 diagrammatically shows an example output of the flow chart of FIG. 3.

Referring now to FIG. 4, an example of the displayed recommendation and map 40 is shown. The map 40 can include for example, a reduced ultrasound scanning scheme (8 ROIs) are shown, one of which can be highlighted (indicated by dashed lines). The recommendation 40 from left to right can include: (a) a 2D projection map with highlighted zone(s), (b) a predetermined track for moving the US probe 20, (c) a table with zones and modes for the ultrasound imaging data 22, (d) a step-by-step indication of the zone and mode for the ultrasound imaging data 22.

Referring back to FIG. 3, at an operation 116, the US imaging device 18 is controlled to acquire one or more US images 22 of at least one of the ROIs displayed on the display device 14 (or the display device 25). In some examples, one or more ROIs in the map 40 can be selected, and the US imaging device 18 is controlled to acquire US images 22 of the patient P corresponding to the selected ROI. In other examples, the patient-specific mechanical ventilation model 36 can be updated using the generated map 40. The acquired US images 22 can then be used as the follow-up US examination for use in updating the model 104, as indicated in FIG. 3 by flowback arrow 117.

For example, the sonographer scans the highlighted zones (or predetermined track) and reports the findings in a table (manually or automated) with a pre-determined format for further processing. For example, a cell "Anterior Inferior" contains three data: "Lung sliding: yes;" "Pleural lines: yes;" and "Lesion: 10 mm." Alternatively, in the case of wiping, the ultrasound probe 20 is registered to the patient's chest and subsequently an image analysis algorithm (e.g., based on machine learning (ML)) automatically analyses the stream of ultrasound images 22 and generates the updates for the model 36 such as a new lesion size. The model 36 can also be updated based on the data table. For example, the lesion size is increased from 8 to 10 mm.

In the course of time, as the model 36 gets more mature, X-ray-based imaging (CT, X-ray) can be reduced, and the use of ultrasound can be increased. This can be done with each new patient, or with a new user for whom X-ray was the clinical reference.

The method 100 can be applied to other clinical domains. It is applicable, whenever it is necessary to track the progress of a patient over time, such as oncology (i.e., to track the effect of treatment (chemotherapy, radiotherapy)), long term lung diseases (e.g., COPD), cardiology and neurology (i.e., to track blood vessels and blood flow, e.g., stenosis, hemodynamic and structural information); and so forth.

The following describes a particular example of the method 100. A patient enters the ICU with Covid-19. A CT scan 32 shows lesions (i.e., bilateral multiple peripheral ground-glass opacities), which can be identified by a radiologist, CT physics, or machine learning (ML). A model 36 is constructed, showing that these lesions have no flow and no deformation. The model 36 then simulates a strain distribution in the lung. Based on the simulation, a therapist sets a PEEP pressure and other settings (volume, oxygen) on the mechanical ventilator 2. The patient responds well (i.e., is stable). A 3D ROI map 40 is constructed based on the simulation (e.g., ROI type 1—the lesions known from the CT scan 32, and ROI type 2: at risk areas without lesions but with a strain value greater than 2). The ROI map 40 is projected in a 2D scanning scheme and shown in the display device 14 or 25. A sonographer scans the highlighted chest areas (e.g., ROI type 1: may have a changed lesion size, ROI type 2: may have initiated a lesion, and so forth). The model 36 is updated (i.e., to include existing lesions and new lesions). The model simulation results are compared with the measurement data from the mechanical ventilator 2 and the optional patient monitor 26. A decision on next imaging modality is made. If the patient is stable or as predicted, ultrasound imaging is selected. If the patient is not stable or if there is a change of greater than 10% between the DT output and the measurements, X-ray or CT is selected because there might be a new lesion at an unexpected location. The decision (i.e., recommendation) is shown in display device 14 or 25.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A mechanical ventilation assessment assistance device, comprising:

at least one electronic processor; and a non-transitory storage medium storing instructions readable and executable by the at least one electronic processor to perform a mechanical ventilation assessment assistance method including:

obtaining an image of a patient (P) receiving mechanical ventilation;

generating or updating a patient-specific lung model of at least one lung of the patient based on the obtained image;

simulating a response of the patient to a mechanical ventilation therapy using the generated or updated patient-specific lung model;

comparing the simulated response with an actual response of the patient to the mechanical ventilation therapy;

based on the comparison, determining an imaging recommendation for acquiring an image of at least one lung of the patient;

outputting the determined imaging recommendation;

generating a map including one or more regions of interest (ROI) in the obtained image when the actual response of the patient (P) to the applied mechanical ventilation therapy satisfies a predetermined criterion; and displaying the generated map on a display device.

2. The device of claim 1, wherein the generating or updating includes:

identifying one or more lung lesions in the obtained image; and generating or updating the patient-specific lung model of the patient (P) including the identified one or more lung lesions.

3. The device of claim 1, wherein the generating or updating includes:

identifying fluid in at least one lung in the obtained image; and generating or updating the patient-specific lung model of the patient (P) including the identified fluid in at least one lung.

4. The device of claim 1, wherein the generating or updating includes:

determining at least one value of at least one biophysical parameter of at least one lung region of the patient (P) using the obtained image; and generating or updating the patient-specific lung model of the patient including the determined at least one value.

5. The device of claim 1, wherein the obtained image includes a spectral computed tomography (CT) or electrical impedance tomography (EIT) image, and the generating or updating includes:

identifying a perfusion distribution in at least one lung of the patient (P) using the obtained spectral CT or EIT image; and generating or updating the patient-specific lung model of the patient including the identified perfusion distribution.

6. The device of claim 1, wherein the determined imaging recommendation is one of:

a recommendation to acquire an ultrasound image of the patient (P) if the comparison of the simulated response with the actual response of the patient to the mechanical ventilation therapy satisfies a predetermined criterion; or a recommendation to acquire a radiation image of the patient otherwise.

7. The device of claim 1, wherein the determining of the imaging recommendation includes:

determining the one or more patient-specific ultrasound imaging settings; and determining a recommendation to acquire an ultrasound image of the patient using the determined one or more patient-specific ultrasound imaging settings.

8. The device of claim 7, wherein the determining of the one or more patient-specific ultrasound imaging settings includes one or more of:

determining one or more spatial locations to be imaged in the acquired ultrasound image of the patient (P).

9. A mechanical ventilation assessment assistance device, comprising:

at least one electronic processor; and a non-transitory storage medium storing instructions readable and executable by the at least one electronic processor to perform a mechanical ventilation assessment assistance method including:

obtaining an image of a patient (P) receiving mechanical ventilation;

generating or updating a patient-specific lung model of at least one lung of the patient based on the obtained image;

simulating a response of the patient to a mechanical ventilation therapy using the generated or updated patient-specific lung model;

comparing the simulated response with an actual response of the patient to the mechanical ventilation therapy;

based on the comparison, determining an imaging recommendation for acquiring an image of at least one lung of the patient;

outputting the determined imaging recommendation;

updating settings of a mechanical ventilator applying the mechanical ventilation therapy to the patient (P) when the actual response of the patient to the applied mechanical ventilation therapy does not satisfy a predetermined criterion; and applying the mechanical ventilation therapy with the updated settings to the patient.

10. The device of claim 1, wherein the instructions further include:

controlling an imaging device to acquire one or more images of at least one of the ROIs displayed on the display device.

11. The device of claim 10, wherein the instructions further include:

receiving, on the display device, one or more inputs indicative of a selection of one of the ROIs; and controlling an imaging device to acquire one or more images of the selected ROI.

12. The device of claim 1, wherein the instructions further include:

updating patient-specific mechanical ventilation model for the patient (P) with the acquired one or more images of at least one of the ROIs.

13. The device of claim 1, wherein the acquired one or more images of at least one of the ROIs comprise ultrasound images.

14. A mechanical ventilation assessment assistance method comprising, with at least one electronic processor:

obtaining an image of a patient (P) receiving mechanical ventilation;

generating or updating a patient-specific lung model of at least one lung of the patient based on the obtained image;

simulating a response of the patient to a mechanical ventilation therapy using the generated or updated patient-specific lung model;

comparing the simulated response with an actual response of the patient to the mechanical ventilation therapy;

based on the comparison, determining an imaging recommendation for acquiring an image of at least one lung of the patient;

outputting the determined imaging recommendation;

generating a map including one or more regions of interest (ROI) in the obtained image when the actual response of the patient (P) to the applied mechanical ventilation therapy satisfies a predetermined criterion; and displaying the generated map on a display device.

* * * * *